(12) United States Patent
Graham

(10) Patent No.: US 8,734,372 B1
(45) Date of Patent: May 27, 2014

(54) SYSTEMS AND METHODS FOR DECOMPRESSION AND ELLIPTICAL TRACTION OF THE CERVICAL AND THORACIC SPINE

(71) Applicant: Richard A. Graham, Sunset Beach, CA (US)

(72) Inventor: Richard A. Graham, Sunset Beach, CA (US)

(*) Notice: Subject to any disclaimer, the term of this patent is extended or adjusted under 35 U.S.C. 154(b) by 0 days.

(21) Appl. No.: 14/085,432

(22) Filed: Nov. 20, 2013

(51) Int. Cl.
*A61F 5/042* (2006.01)
*A61H 1/02* (2006.01)

(52) U.S. Cl.
USPC ............. 602/32; 602/13; 602/18; 606/240; 5/636; 5/655.3

(58) Field of Classification Search
USPC ........... 602/13, 18, 32–39; 5/636–638, 655.3; 601/39, 148–152; 606/237–241
See application file for complete search history.

(56) References Cited

U.S. PATENT DOCUMENTS

| | | |
|---|---|---|
| 2,806,471 A | 9/1957 | Breese |
| 3,521,623 A | 7/1970 | Nichols et al. |
| 3,667,457 A | 6/1972 | Zumaglini |
| 3,765,412 A | 10/1973 | Ommaya et al. |
| 3,899,797 A | 8/1975 | Gunst |
| 3,974,827 A | 8/1976 | Bodeen |
| 4,024,861 A | 5/1977 | Vincent |
| D247,312 S | 2/1978 | Zeiss |
| 4,114,611 A | 9/1978 | Lyle et al. |
| 4,135,503 A | 1/1979 | Romano |
| 4,159,020 A | 6/1979 | von Soiron et al. |
| 4,161,946 A | 7/1979 | Zuesse |
| 4,194,501 A | 3/1980 | Watt |
| 4,391,466 A | 7/1983 | Smith |
| 4,583,255 A | 4/1986 | Mogaki et al. |
| 4,583,532 A | 4/1986 | Jones |
| 4,669,455 A | 6/1987 | Bellati |

(Continued)

FOREIGN PATENT DOCUMENTS

| | | |
|---|---|---|
| DE | 2638077 | 3/1977 |
| JP | 404327849 | 11/1992 |

(Continued)

OTHER PUBLICATIONS

Cailliet, R., M.D., Low Back Pain Syndrome, Edition 4, Pain Series, Copyright 1994 [1A] p. 5, [1B] pp. 6-8, [1C] pp. 6-8.

(Continued)

*Primary Examiner* — Patricia Bianco
*Assistant Examiner* — Kari Petrik
(74) *Attorney, Agent, or Firm* — Knobbe Martens Olson & Bear, LLP

(57) ABSTRACT

A traction device comprises a frame, a first bladder portion, a second bladder portion, a strap, and a pump. The first bladder expands in an outward direction a distance greater than in a transverse direction. The second bladder expands in an angular direction. The second bladder is positioned generally below and to the side of the first bladder. The frame is secured to the user's head. Upon expanding in the outward direction, the first bladder bears against the back of the user's neck and forces the cervical spine to curve forwardly. Upon expanding in the transverse direction, the first bladder applies an angular traction to the cervical spine. Upon expanding in the angular direction, the second bladder bears angularly against the back of the user's upper thoracic region and forces the thoracic spine to decompress and reduces hyper-kyphosis of the upper thoracic spine.

11 Claims, 10 Drawing Sheets

(56) References Cited

U.S. PATENT DOCUMENTS

| | | | |
|---|---|---|---|
| 4,736,736 A | 4/1988 | Moers et al. | |
| RE32,791 E | 11/1988 | Saunders | |
| 4,805,603 A | 2/1989 | Cumberland | |
| 4,838,613 A | 6/1989 | Smith | |
| D302,592 S | 8/1989 | Holmes | |
| 4,981,131 A | 1/1991 | Hazard | |
| 4,995,378 A | 2/1991 | Dyer et al. | |
| 5,003,968 A | 4/1991 | Mars | |
| 5,062,414 A | 11/1991 | Grim | |
| 5,067,483 A | 11/1991 | Freed | |
| 5,070,865 A | 12/1991 | Iams | |
| 5,147,287 A | 9/1992 | Jewell et al. | |
| 5,154,186 A | 10/1992 | Laurin et al. | |
| 5,181,904 A | 1/1993 | Cook et al. | |
| 5,190,348 A | 3/1993 | Colasanti | |
| 5,201,761 A | 4/1993 | Serola | |
| 5,207,716 A | 5/1993 | McReynolds | |
| 5,211,162 A | 5/1993 | Gillen, Jr. et al. | |
| 5,232,424 A | 8/1993 | Pearson et al. | |
| 5,279,310 A | 1/1994 | Hsien | |
| 5,292,175 A | 3/1994 | Artz | |
| 5,305,750 A | 4/1994 | Makita | |
| 5,338,276 A | 8/1994 | Jull et al. | |
| 5,382,226 A | 1/1995 | Graham | |
| 5,403,266 A | 4/1995 | Bragg et al. | |
| 5,410,472 A | 4/1995 | Anderson | |
| 5,423,861 A | 6/1995 | Kelley | |
| 5,472,401 A | 12/1995 | Rouillard et al. | |
| 5,560,056 A | 10/1996 | Tai | |
| 5,562,324 A | 10/1996 | Massara et al. | |
| 5,569,176 A | 10/1996 | Graham | |
| 5,713,841 A * | 2/1998 | Graham | 602/32 |
| 5,738,640 A * | 4/1998 | Carlson-Orsi | 602/19 |
| 5,772,281 A | 6/1998 | Massara | |
| 5,906,586 A | 5/1999 | Graham | |
| 5,933,890 A | 8/1999 | Codd | |
| 6,039,737 A | 3/2000 | Dyer | |
| D445,505 S | 7/2001 | Shapiro | |
| 6,305,040 B1 | 10/2001 | Myler | |
| 6,506,174 B1 | 1/2003 | Saunders et al. | |
| 6,592,184 B1 | 7/2003 | Segal et al. | |
| D486,235 S | 2/2004 | Haddock | |
| 6,899,690 B2 | 5/2005 | Saunders et al. | |
| D508,566 S | 8/2005 | Graham et al. | |
| 7,022,094 B2 | 4/2006 | Buckman et al. | |
| 7,060,085 B2 | 6/2006 | Graham et al. | |
| 7,108,671 B2 | 9/2006 | Saunders et al. | |
| 7,566,314 B2 | 7/2009 | Saunders et al. | |
| 8,029,453 B2 | 10/2011 | Graham | |
| 8,083,705 B2 | 12/2011 | Saunders et al. | |
| 8,100,846 B1 * | 1/2012 | LaMonica | 602/32 |
| 2003/0088200 A1 | 5/2003 | Saunders et al. | |
| 2004/0143206 A1 | 7/2004 | Saunders et al. | |
| 2006/0161087 A1 | 7/2006 | Carter et al. | |
| 2006/0206046 A1 | 9/2006 | Saunders et al. | |
| 2007/0079415 A1 | 4/2007 | Carlson | |
| 2009/0118657 A1 | 5/2009 | Saunders et al. | |
| 2009/0187127 A1 | 7/2009 | Buckman et al. | |

FOREIGN PATENT DOCUMENTS

| | | |
|---|---|---|
| WO | WO 87/00424 | 1/1987 |
| WO | WO 96/14810 A2 | 5/1996 |
| WO | WO 96/14810 A3 | 8/1996 |

OTHER PUBLICATIONS

Donald D. Harrison, Ph.D., M.S., D.C., The Physics of Spinal Correction Copyright 1994 [2A] Fig. 3-3. [2B] Fig 1-21. [2C] Fig 3-3 and Fig 7-6, [2D] Fig 3-6., [2E] Figures 7-2,7-3.

Kirkaldy-Willis, M.A., M.D., F.R.C.S., (Edin), F.A.C.S., Managing Low Back Pain, Copyright 1988, [3A] p. 306.

Alf Breig, M.D. Adverse Mechanical Tension in the Central Nervous System Copyright 1978 p. 17 figure A and B [4A].

Norman Shealy, M.D., Ph.D. 2006 IRB Approved Study of Cervical Decompression Treatment, Copyright 20008, Practical Pain Management Apr. 2007.

Norman Shealy, M.D., Ph.D. 2008 IRB Approved MRI Study of the Effects of Axial Linear Traction and Expanding Ellipsoidal Decompression (EED®) via Posture Pump® on Cervical Curve, Disc Protrusions and Disc Height, Copyright 2008, Practical Pain Management Mar. 2010.

* cited by examiner

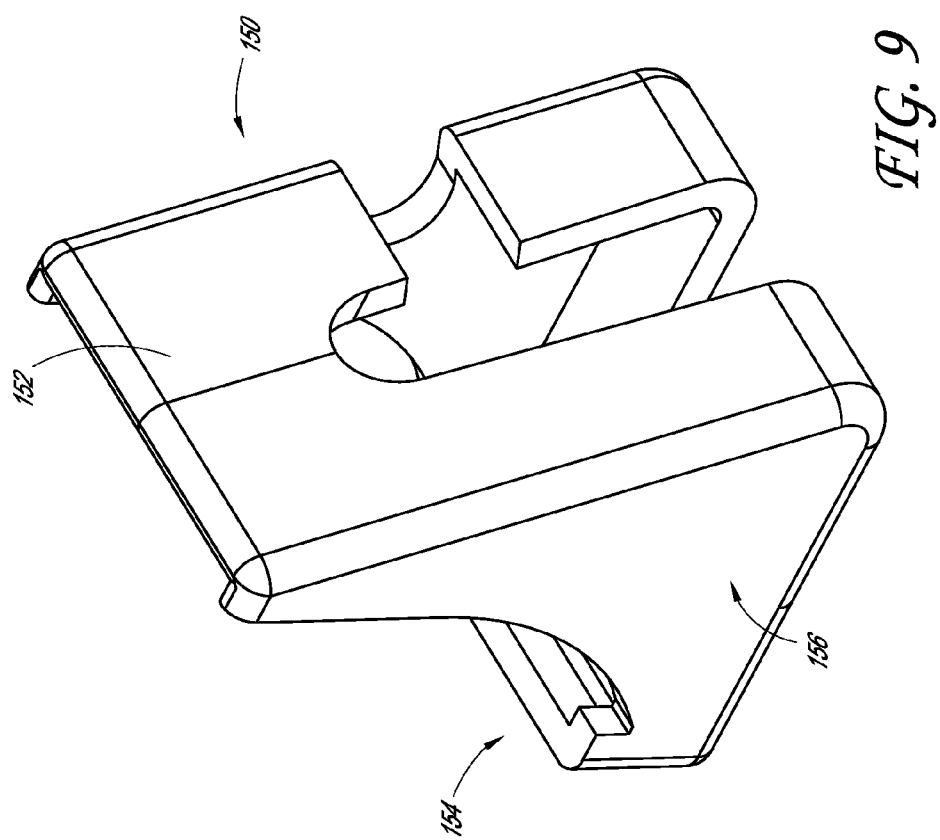

SYSTEMS AND METHODS FOR DECOMPRESSION AND ELLIPTICAL TRACTION OF THE CERVICAL AND THORACIC SPINE

CROSS-REFERENCE TO RELATED APPLICATIONS

Any and all applications for which a foreign or domestic priority claim is identified in the Application Data Sheet as filed with the present application, are hereby incorporated by reference under 37 CFR 1.57.

BACKGROUND

1. Field of the Invention

Disclosed herein are spinal decompression and traction systems and methods related to the field of spinal treatment. More particularly, certain embodiments disclosed herein relate to cervical and thoracic spinal decompression and traction systems having a plurality of inflatable bladders and methods of use that maintain a normal lordotic curve and counter hyper-kyphosis of the upper thoracic spine.

2. Description of the Related Art

Cervical pain is one of the most common health-related complaints. When there are no neurological deficits, symptomatic relief of pain is often sought with either non-steroidal analgesics, or various physical therapy modalities, including cervical traction. Most traction has consisted of axial linear distraction employing various head/chin straps and weights of 20 to 25 pounds. Such traction tends to straighten the cervical spine and often results in TMJ pain.

The undamaged cervical spine normally defines a forward or lordotic curve of about 43° (measured from C2-C7) whereby weight is distributed on hard individual bony articular surfaces in the posterior and soft intervertebral discs to the anterior. Without such a forward curve in the cervical spine, weight of the head transfers forward onto the soft non-bony intervertebral discs and vertebral bodies causing discs to dehydrate, wear, degenerate and protrude into the anterior subarachnoid space. As vertebral bodies bear uneven stress, spurs and osteophytes form. Additionally, individuals with lost or reversed (buckled) cervical spinal curves eventually exhibit a significant loss of natural joint movement, further limiting the normal canaliculus seepage and imbibition of adjacent fluids via vertebral end plates and annuli. Without such nutrient rich fluids the discs continue to dehydrate, further weakening the discs, resulting in a further loss of mobility, degeneration and possible nerve damage. Active nutrient transport is particularly important because the intervertebral discs' indigenous vascular supply often disappears at approximately 20 years of age.

Further, as the cervical spine is forced into flexion and the lordotic curve is reversed, the dura, cord and nerve-roots are drawn out; the root-sleeves come into contact with the pedicles, and the nerve roots with the inner surfaces of the sleeves. During extension (lordotic curve recovery) the dura, cord and nerve-roots in the cervical canal are slack; the root-sleeves have lost contact with the pedicles and the nerve-roots with the inner surfaces of the sleeves.

Axial/Linear/Longitudinal traction has long been employed to decompress cervical joints of the spine. Typically the head is pulled, pried, lifted or otherwise separated from the thorax along the Y axis (+Y axis translation or elevation translation). Ostensibly, to pry the joints apart at the posterior, forward flexion (+X axis rotation) is often employed in conjunction with or as an unavoidable component of linear traction. Linear traction or elevation translation applied to a curved column decreases or removes the curve. Likewise, adding the component of flexion or + rotation about the X axis, would apply a buckling force to the cervical spine and have the effect of reversing the curve (−Z axis translation). These forces, powerful enough to separate the spinal joints, are unfortunately antithetical to the natural geometry and biomechanics of the human cervical spine. The anchor points commonly used in Axial/Linear/Longitudinal traction are the head as it is pulled away from the thorax and/or the trapezius muscles as the thorax is pushed away from the restrained head. U.S. Pat. No. 4,805,603 to Cumberland describes a method where the head and thorax are separated by two platforms with an expanding air chamber between the two platforms. These methods, due to their linear function reduce, remove or reverse the proper cervical curve. U.S. Pat. No. 6,506,174 to Saunders also describes a linear traction system.

Some alternatives to axial/linear/longitudinal traction for disc, joint and nerve decompression seek to maintain a normal lordotic curve. For example, U.S. Pat. Nos. 5,382,226; 5,569,176; 5,713,841; 5,906,586; 7,060,085; 8,029,453; and D508,566S to Graham, each of which is hereby incorporated by reference herein in its entirety, disclose some embodiments of systems for decompression. In two IRB studies utilizing multiple MRI's, an embodiment of the disclosed systems showed a consistent ability to draw bulging disc material back toward the disc proper and away from the subarachnoid space and spinal cord while simultaneously enhancing or restoring the cervical lordotic curve during and after one 20 minute treatment. Patients reported immediate symptomatic relief of cervical pain. However, there exists a need for improved decompression systems that also address hyper-kyphosis of the upper thoracic spine.

SUMMARY

Described herein are some embodiments of decompression and traction systems that maintain a normal lordotic curve and counter hyper-kyphosis of the upper thoracic spine. Methods of assembling and using the decompression and traction systems described herein are also included. These decompression and traction systems and related methods are described in greater detail below.

One aspect of the present invention is the recognition that traditionally available traction systems do not provide devices, systems and methods that simultaneously address cervical lordotic curve loss/reversal (hypolordosis/kyphosis), and the often accompanying posterior (−Z) translation (hyper-kyphosis) of the upper thoracic spine. Embodiments and methods described herein preferably provide pneumatic radial decompression and traction equipment for treatment of the cervical and thoracic spine including a free-standing frame, first and second expandable bladders, the first expandable bladder providing positive pressure to support a cervical spinal portion in a normal lordotic curve configuration, and the second expandable bladder providing positive pressure to support a thoracic spinal portion in a normal curve configuration to counter hyper-kyphosis of the upper thoracic spine.

According to certain embodiments of the invention, devices, systems and methods are described that simultaneously address cervical lordotic curve loss/reversal (hypolordosis/kyphosis), and the often accompanying posterior (−Z) translation (hyper-kyphosis) of the upper thoracic spine.

In relation to the head and neck, −Z translation of the upper thoracic spine is an integral part of anterior or "Forward Head Carriage." As the head shifts forward and/or the upper thoracic spine moves posterior, the weight of the head and neck, approximately 15 pounds, creates a forward buckling force (−Y and +Z combination) on the thoracic spine. This continuous forward and downward force begets more forward head carriage and more compressive action to the cervical and thoracic intervertebral discs and bodies. Many are familiar with the term "Dowagers Hump" where hyper kyphosis of the thoracic spine is so pronounced as to be obvious with the naked eye. While approximately 30% of these postural defects (especially in women) are said to be caused by anterior thoracic vertebral body fractures due to osteoporosis, most hyper-kyphotic postures are developed over time by continuous anterior and downward force on the cervical and thoracic intervertebral discs and vertebral bodies.

As people spend long hours crouched in front of computer screens, wear heavy back packs, are involved whiplash type auto and sports injuries, forward head posture with associated cervical curve loss, and hyper thoracic kyphosis has become more prevalent. Neck and back pain, muscle tension and spasm, headaches, neuropathies and degenerative vertebral joint disease result from continuous cervical-thoracic disc and joint compression. While there have been elastic bands and braces applied to the spine to pull or hold it upright in an attempt to ameliorate worsening posture, results are mixed.

In some embodiments, the devices, systems and methods described herein apply pneumatic forces directly to the offending spinal apexes in opposing directions. With the simultaneous application of two separate air cells the cervical spine is locked and powerfully decompressed into its proper lordotic or curved configuration (<Λ>) with −Y +Z +Y force vectors while the hyper kyphotic area of the upper thoracic spine is simultaneously decompressed with a combination +Z/−Y force mid-vector. The cervical spine's lordotic curve is powerfully decompressed and enhanced while the thoracic hyper-kyphosis is simultaneously reduced. In some embodiments, a two pump system can be employed to alternate or unevenly inflate the air cells. In some embodiments, a complex multi vectored air cell can be used in place of two individual cells. In some embodiments, the devices, systems and methods described herein use the entire cervical spine including the occiput (base of skull) as the 1st anchor point and the upper thoracic spine as the second point. The air cells can directly contact the cervical spine/occiput and the upper 25% of the thoracic spine.

According to one embodiment, a traction device comprises a frame, a first bladder portion, a second bladder portion, a strap, and a pump. The first bladder expands in an outward direction a distance greater than in a transverse direction. The second bladder expands in an angular direction. The second bladder is positioned generally below and to the side of the first bladder. The frame is secured to the user's head. Upon expanding in the outward direction, the first bladder bears against the back of the user's neck and forces the cervical spine to curve forwardly. Upon expanding in the transverse direction, the first bladder applies an angular traction to the cervical spine. Upon expanding in the angular direction, the second bladder bears angularly against the back of the user's upper thoracic region and forces the thoracic spine to decompress and reduces hyper-kyphosis of the upper thoracic spine.

In certain embodiments, a traction device for imparting a forward curve to the cervical spine and reducing hyper-kyphosis of the upper thoracic spine is provided. The device comprises a frame adapted to be supported on a rigid support surface. The frame is configured to be disposed about a user's head and neck and defines contact surfaces for abutting the rigid support surface. The frame has a neck support extending between first and second side portions of the frame. A first inflatable elongated bladder is coupled to the neck support and configured to be positioned below a neck of a user during use. The first inflatable elongated bladder is expandable in a first direction outwardly from the neck support toward the neck of a user and expandable in a second direction substantially normal to the first direction upon inflation. A second inflatable elongated bladder is coupled to the neck support and configured to be positioned below the upper thoracic region of a user during use. The second inflatable elongated bladder is expandable in a third direction angularly from the neck support toward the upper thoracic spine of a user upon inflation. A securing strap is coupled to the frame and configured to secure the frame to the user's head such that the first inflatable elongated bladder is disposed adjacent the back of the user's neck and transverses the cervical spine such that the first direction of expansion is toward and substantially normal to the cervical spine. The second inflatable elongated bladder is disposed adjacent the back of the user's upper thoracic region and transverses the upper thoracic spine such that the third direction of expansion is toward and substantially normal to the upper thoracic spine. A pump system is provided for selectively inflating and deflating the first and second inflatable elongated bladders. Upon the first inflatable bladder expanding in the first direction, the first inflatable bladder bears outwardly against the back of the user's neck and forces the cervical spine to curve forwardly. Upon expanding in the second direction, the first inflatable bladder applies an angular traction to the cervical spine. Upon the second inflatable bladder expanding in the third direction, the second inflatable bladder bears angularly against the back of the user's upper thoracic region and forces the thoracic spine to decompress and reduces hyper-kyphosis of the upper thoracic spine.

In some embodiments, the traction device comprises a valve positioned in communication with the pump system and the first and second inflatable elongated bladders. The valve comprises varying lumen diameters that direct flow between the pump system and the first and second inflatable elongated bladders. The first inflatable elongated bladder is pivotably coupled to the neck support. A spacer is configured to be coupled between a portion of the frame and the second inflatable elongated bladder to adjust the angulation of the second inflatable elongated bladder during inflation.

In other embodiments, a traction device is provided for imparting a forward curve to the cervical spine and reducing hyper-kyphosis of the upper thoracic spine. The device comprises a frame having a transverse neck support projecting upwardly from first and second side portions defining a base of the frame. A first inflatable bladder portion is coupled to the neck support. The first inflatable bladder portion is configured to expand in an outward direction from the neck support a distance greater than the expansion of the first inflatable bladder portion in a transverse direction normal thereto. A second inflatable bladder portion is coupled to the neck support. The second inflatable bladder portion is configured to expand in an angular direction from the neck support. The second inflatable bladder portion is positioned generally below and to the side relative to the first inflatable bladder portion. A strap is coupled to the frame and configured to secure the frame to the user's head such that the first inflatable bladder portion is disposed adjacent the back of the user's neck and transverses the cervical spine such that the outward direction of expansion is toward and substantially normal to the cervical spine. The second inflatable bladder portion is disposed adjacent the back of the user's upper thoracic region and transverses the upper thoracic spine such that the angular direction of expansion is toward and substantially normal to the upper thoracic spine. A pump system is provided for inflating the first and second inflatable bladder portions. Upon the first inflatable bladder portion expanding in the outward direction, the first inflatable bladder portion bears outwardly against the back of the user's neck and forces the cervical spine to curve forwardly. Upon expanding in the transverse direction, the first inflatable bladder portion applies an angular traction to the cervical spine. Upon the second inflatable bladder portion expanding in the angular direction, the second inflatable bladder portion bears angularly against the back of the user's upper thoracic region and forces the thoracic spine to decompress and reduces hyper-kyphosis of the upper thoracic spine.

In some embodiments, a method is provided for imparting a forward curve to the cervical spine and reducing hyper-kyphosis of the upper thoracic spine. The method comprises securing a traction device to a user's head. The traction device comprises a support frame having a transverse neck support projecting upwardly from a base of the support frame and first and second inflatable bladder portions coupled to the neck support. The traction device is secured to the user's head includes positioning the traction device such that the first inflatable bladder portion transverses the cervical spine, and such that the second inflatable bladder portion transverses the upper thoracic spine. The first inflatable bladder portion is expanded in a direction outward from the neck support and toward and substantially normal to the cervical spine to force the cervical spine to curve forwardly. The first inflatable bladder portion is expanded in a transverse direction to apply an angular traction to the cervical spine. The second inflatable bladder portion is expanded in a direction toward and substantially normal to the upper thoracic spine to force the upper thoracic spine to decompress and reduce hyper-kyphosis of the upper thoracic spine.

In certain embodiments, methods may comprise alternately inflating and deflating the first and second bladder portions. Inflation and deflation of the first and second bladder portions can be repeated. The first inflatable bladder portion can have a semi-ellipsoidal configuration upon inflation. The second inflatable bladder portion can have a semi-ellipsoidal configuration upon inflation. During inflation or deflation, flow can be directed between the pump system and the bladder portion through a valve that comprises different lumen diameters to provide particular flow to or from the first and second inflatable bladder portions. Methods can include pivoting the first inflatable bladder relative to the neck support and/or positioning a spacer between a portion of the frame and the second inflatable bladder portion to adjust the angulation of the second inflatable bladder portion during inflation.

These and other objects and advantages of the present disclosure will become readily apparent from the following detailed description taken in conjunction with the accompanying drawings.

BRIEF DESCRIPTION OF THE DRAWINGS

FIG. 9 is a perspective view of the spacer component shown in FIG. 8.

DETAILED DESCRIPTION

Figure 1:
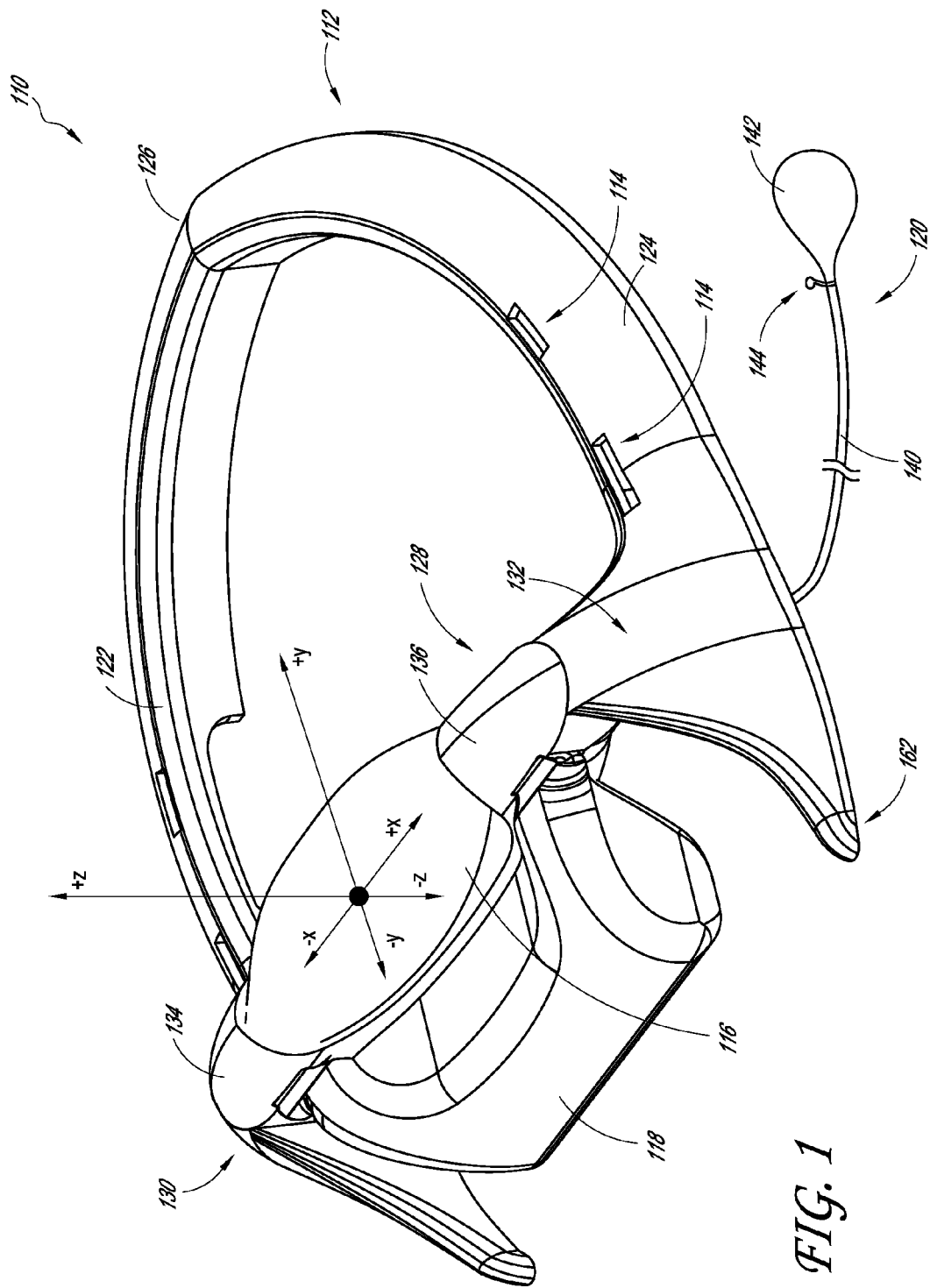
FIG. 1 is a perspective view of one embodiment of a decompression and traction system.
Figure 2:
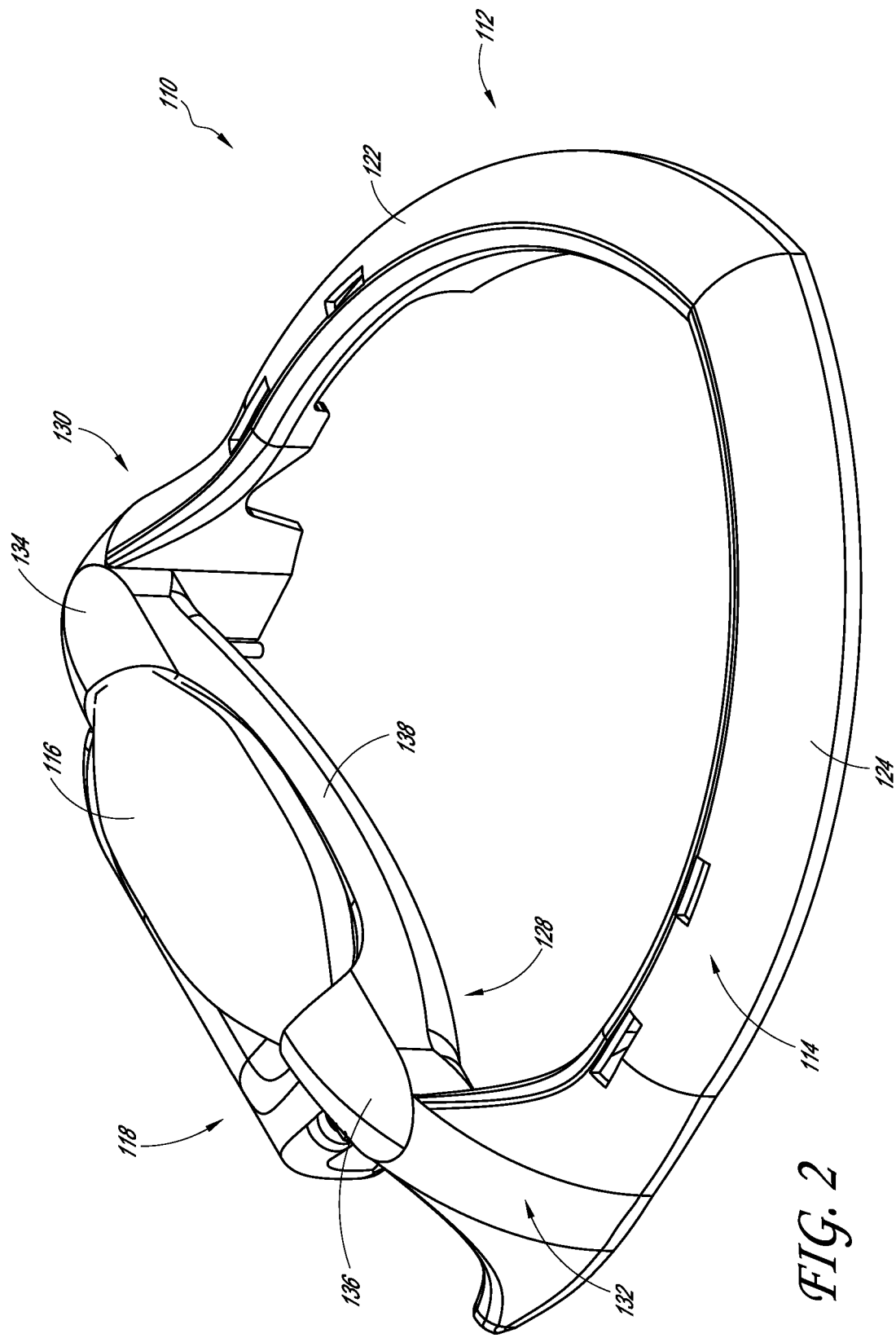
FIG. 2 is a perspective view of a portion of the system shown in FIG. 1.
Figure 3:
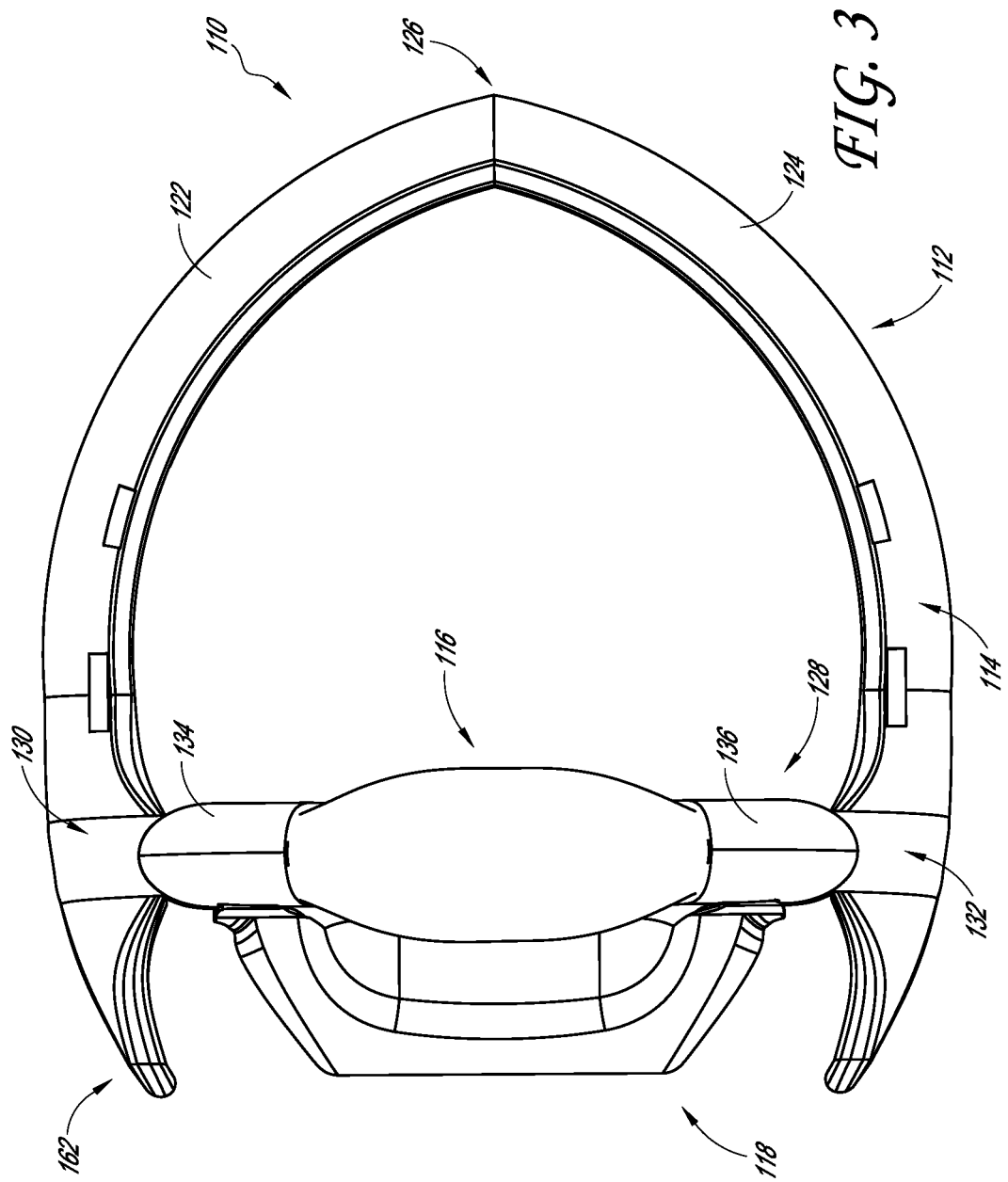
FIG. 3 is a top view of a portion of the system shown in FIG. 1.
Figure 4:
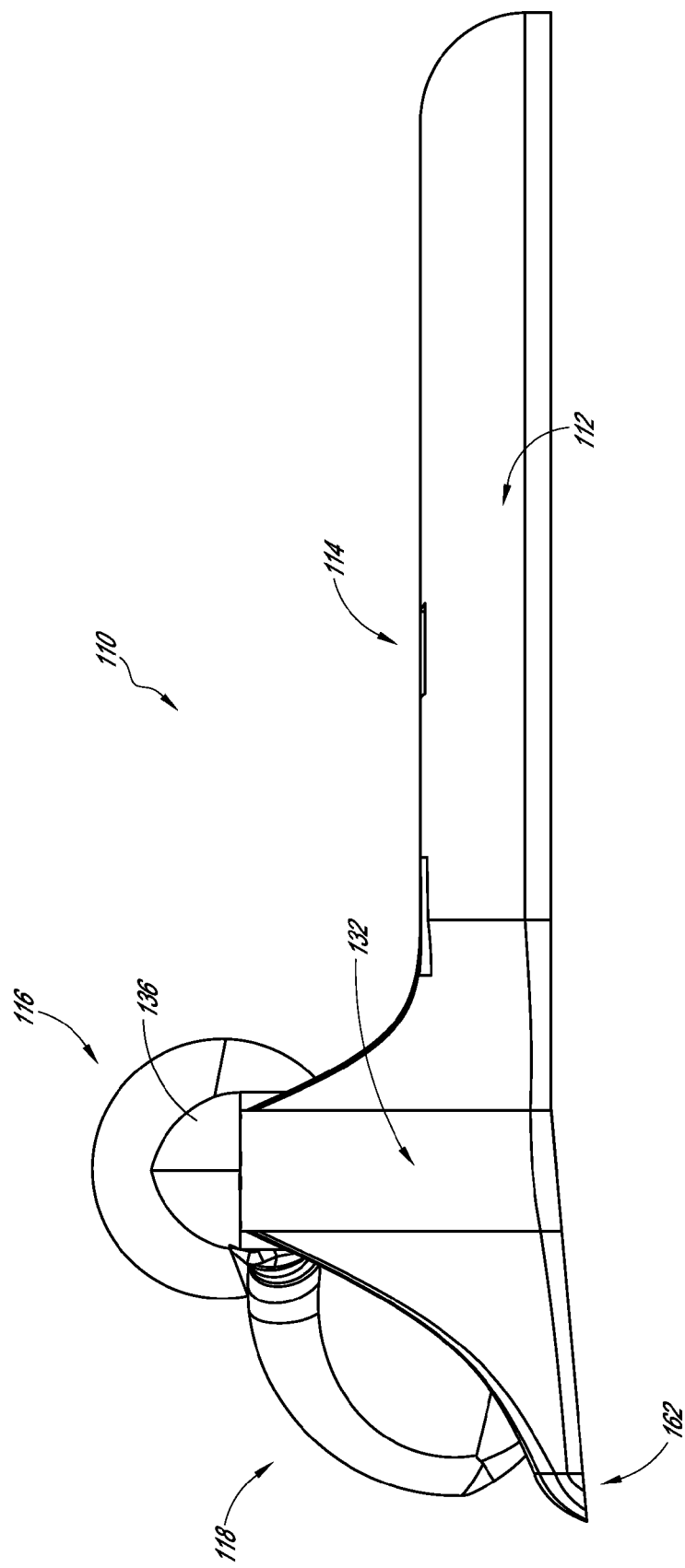
FIG. 4 is a side view of a portion of the system shown in FIG. 1.
Figure 5:
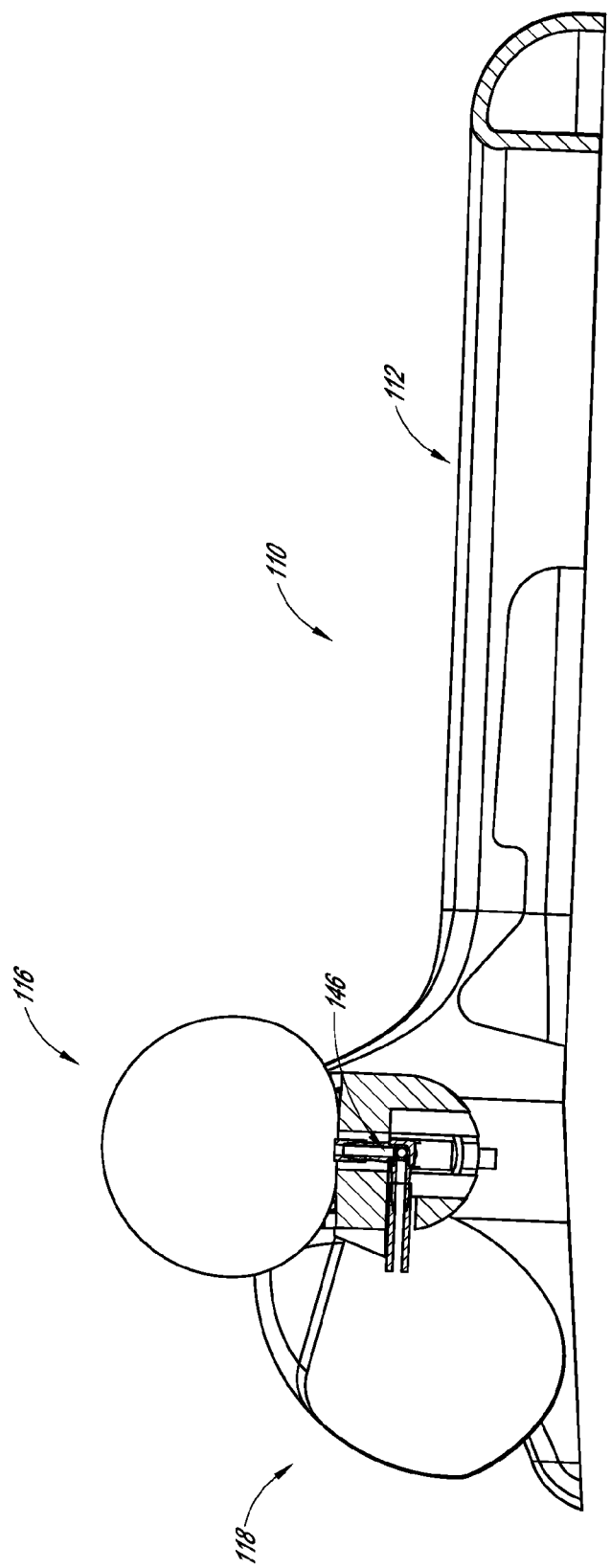
FIG. 5 is a cross-sectional side view of a portion of the system shown in FIG. 1.

According to some preferred embodiments, the devices, systems and methods described herein relate to a decompression and traction system for imparting the desired lordotic shape into the cervical region of the spine and counteracting hyper-kyphosis of the area of the upper thoracic spine. Some systems can be used to work the spine and surrounding tissue to promote fluid and cellular exchange in and around the intervertebral discs.

In some embodiments, the device comprises a frame, a first substantially ellipsoidal inflatable bladder transversely in a neck support cradle carried by the frame, a second inflatable bladder supported on the neck support cradle carried by the frame and configured to provide a force vector against the upper thoracic spine when inflated, one or more restraining straps for securing the device to the user's head such that the first and second bladders are disposed against the back of the neck under a stress point in the cervical spine and against the hyper-kyphotic upper thoracic spine, respectively. Controlled inflation of the bladders by the user by a hand-held pump causes a controlled lifting and a stretching of the cervical and thoracic spine. As the first bladder is inflated, the configuration of the first bladder causes the first bladder to expand vertically and, to a lesser extent, transversely. The vertical expansion lifts the spine, creating a spinal apex while the transverse expansion of the bladder applies an angular traction to the neck on both sides of the apex. As the second bladder is inflated, preferably simultaneously, the configuration of the second bladder causes the second bladder to expand vertically and transversely. The vertical and transverse expansion lifts the spine and applies an angular traction to the thoracic region.

By controlling the inflation of the bladders, the user can control the lifting and stretching of the spine and incrementally increase the magnitude of spinal arc and decompression of the cervical and thoracic regions to his or her own tolerance. As the bladders are repetitively inflated to the tolerance of the user and deflated, the cervical spine is alternatively and actively forced from a lesser arc to a greater or hyper-lordotic arc and the hyper-kyphotic arc of the upper thoracic spine is simultaneously reduced and decompressed, thereby promoting nutrient transport to the intervertebral discs while simultaneously increasing the cervical lordotic arc and decreasing the thoracic hyper-kyphosis. These decompression and traction systems and related methods are described in greater detail below.

Referring now to the drawings, as shown in FIGS. 1-5, according to one embodiment, a traction device 110 comprises a frame 112, openings or slots 114 configured to receive one or more straps to restrain the forehead and/or chin of a user, a first inflatable air bladder 116, a second inflatable air bladder 118, and an air pump assembly 120.

The frame 112 is preferably molded of a durable plastic material in a tubular configuration so as to define a pair of side members 122 and 124 curved and meeting at an apex 126, and a transverse neck support 128. The frame side members 122 and 124 preferably form a stable base. The neck support 128 preferably comprises vertically extending portions 130 and 132 which project upwardly from the side members 122 and 124 respectively and project inwardly to define inwardly directed raised lateral portions 134 and 136. A neck cradle 138 extends transversely between portions 134 and 136, spanning frame side members 122 and 124. In some embodiments, the frame can be provided with side members that are not connected at an apex 126, such as in some embodiments where side members are shorter.

The first and second air bladders 116 and 118 are preferably configured for inflation and simultaneous application of force to the cervical and thoracic spine, when the patient is in a treatment position, to decompressed the spine into its proper lordotic or curved configuration (<Λ>) with −Y +Z +Y force vectors being applied to the cervical spine while the hyperkyphotic area of the upper thoracic spine is simultaneously decompressed with a combination +Z/−Y force mid-vector. The cervical spine's lordotic curve is powerfully decompressed and enhanced while the thoracic hyper-kyphosis is simultaneously reduced. In some embodiments, the devices, systems and methods described herein use the entire cervical spine including the occiput (base of skull) as the 1st anchor point and the upper thoracic spine as the second point. The air cells can directly contact the cervical spine/occiput and the upper 25%-40% of the thoracic spine. The first and second inflatable bladders 116, 118, are described in more detail below.

Figure 6:
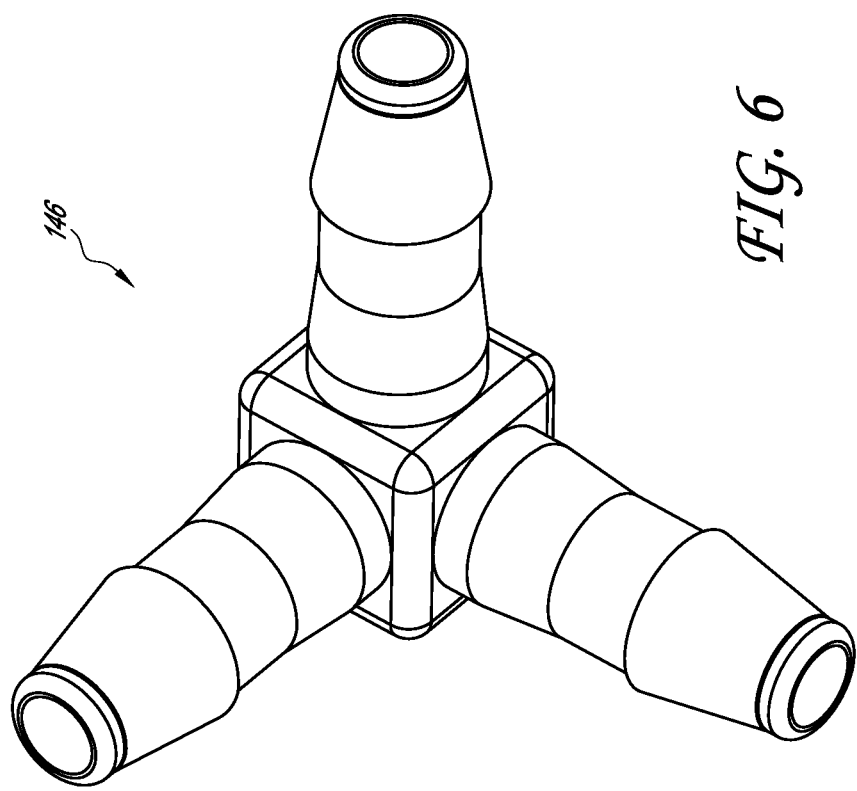
FIG. 6 is a perspective view of a valve component shown in the cross-sectional side view of FIG. 5.

To provide selective inflation and deflation of the first and second inflatable bladders 116, 118, a flexible air line 140 of the air pump assembly 120 communicates the interior of the first and second inflatable bladders 116, 118 with a hand-operated air pump 142. In other embodiments an automated pump can be used. A pressure relief valve 144 is preferably disposed between the air line 140 and pump 142. Air line 140 preferably extends from the relief valve 144 through an opening in the neck support 128 and communicates with the first and second inflatable bladders 116, 118. In some embodiments, the air can be communicated through openings formed in the underside or ends of the bladders. In some embodiments, a valve 146, such as a multi-directional metering valve, shown in FIGS. 5 and 6 for example, can be coupled with the air line 140 and can direct air to the first and second inflatable bladders 116, 118. In some embodiments the valve 146 comprises different lumen diameters to vary the air flow directed to the opposing traction air cells of the first and second inflatable bladders 116, 118. Different valve components can be used to adjust the amount or flow of air to the respective air cells. While air is an example fluid used in the pneumatic decompression described herein, other suitable fluids can be used to increase or decrease the volume of the bladders, including using liquids in some embodiments. In some embodiments, a two pump system can be employed to alternate or unevenly inflate the air cells. In some embodiments, a single complex multi-vectored cell or bladder can be used in place of two individual cells.

According to one embodiment, by way of example, a frame 112 of a traction device 110 defines a spacing of about nine inches between the curved side members 122 and 124 at a wide portion with the side members coming together at the apex 126 of the frame. The frame 112 is preferably between about 11 to 17 inches in length in some embodiments. The frame 112 preferably elevates the neck support 128 about 0.5 to about 1.5 inches above the floor or surface. In such a configuration, the frame 112 preferably bears against the floor or surface during use and reduces the tendency of the frame to twist about its transverse axis. The cradle 138 in neck support 128 preferably tapers from an elevation of about 3 inches above the floor proximate side members 122 and 124 to a central elevation of about 2.5 inches.

The first expandable bladder 116 is preferably coupled to and carried by the neck support 128 in the cradle 138 defined therein. The first expandable bladder 116 is preferably secured in place as will be described further herein. The lateral portions 134 and 136 of neck support 128 are preferably provided with oppositely facing recesses formed therein adjacent the lateral ends of cradle 138 for receiving the extended ends of the first expandable bladder 116 to facilitate retention and alignment of the bladder on the cradle 138.

According to some embodiments, the upper portion of the first expandable bladder 116 is of a generally semi-ellipsoidal configuration having relatively pointed ends similar to the upper half of a football bladder. In one preferred bladder configuration, the underside of the first expandable bladder 116 is formed with undercut portions so as to define a central depending portion. At least a portion of the cradle is preferably configured to receive the underside of the first expandable bladder 116. Preferably, the first expandable bladder 116, when inflated, will expand upwardly from the cradle 138 to a slightly greater extent than in a transverse direction. Additionally, in some embodiments, provision of the depending portion on the underside of the bladder provides a cushioning effect under the apex of the expanded bladder which bears against the user's neck, making the device more comfortable for the user. Thus, as the bladder is inflated under and against the user's neck, it expands vertically and transversely, lifting the spine to create a spinal apex and applying an angular traction to the neck on both sides of the spinal apex. The amount of traction exerted in the vertical direction, however, will be somewhat greater than that exerted longitudinally to obtain the vertical lift necessary to restore the normal lordotic shape to the cervical region of the spine without overly tractioning the neck longitudinally.

In some embodiments, the first inflatable bladder 116 is constructed of an expandable material such as neoprene rubber, defines a length of between about 8 to 10 inches, a height of about 3 to 4 inches in an uninflated state, and depending on the configuration of the bladder a transverse width of about 3 inches. In some embodiments, the bladder 116 is constructed of a material that resists expansion. In some embodiments, the bladder 116 is constructed of a heat-sealable urethane with 200 Denier nylon. The bladder 116 can comprise a cover of any suitable material, including, for example, a neoprene material. The semi-ellipsoidal upper portion of the first inflatable bladder 116, when inflated, defines a transverse arc of about 4 inches in length about the center of the bladder. It is to be understood that these dimensions are by way of example only and can be varied, as can the configuration of the frame, straps, and first and second bladders without departing from the spirit and scope of the invention. For example, in some embodiments the bladder 116 can have a length of between about 6 to 9 inches, a height of about 2 to 3 inches in a deflated state, a height of about 3 to 4 inches in an inflated state. In some embodiments a deflated circumference of the bladder is about 4 inches and an inflated circumference of the bladder is between about 7 and 8 inches. In an inflated configuration, the bladder 116 can be taller than it is wide, for example, it can be approximately 4 inches tall and approximately 3 inches wide when inflated in some embodiments.

Figure 7:
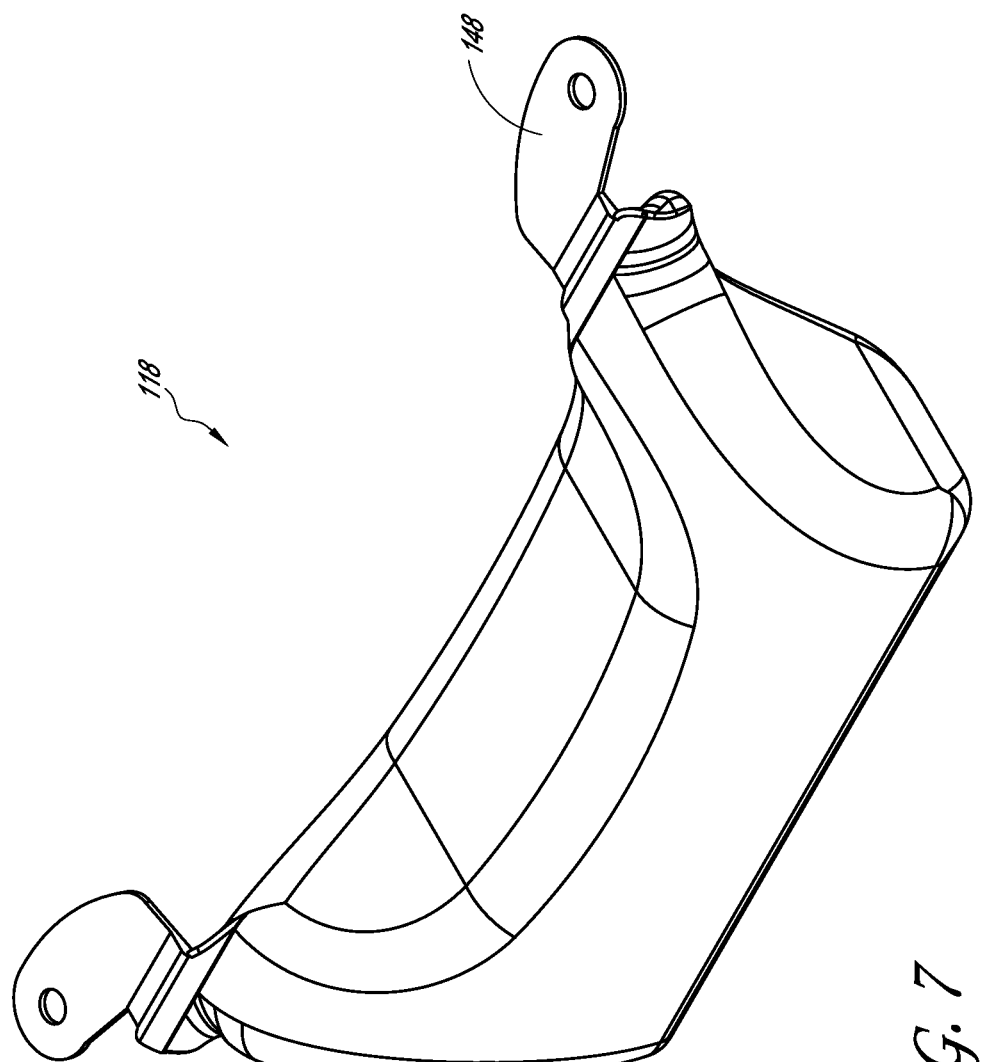
FIG. 7 is a perspective view of a portion of the system shown in FIG. 1, showing a second inflatable bladder in an unassembled configuration.

The second expandable bladder 118 is coupled to and carried by the neck support 128. The second expandable bladder 118 is preferably adjustable in some embodiments to accommodate patient anatomy and align with desired force vector directions as will be described further herein. The lateral portions 134 and 136 of neck support 128 are preferably configured with recesses formed therein for receiving the extended ends 148, shown in FIG. 7, of the second expandable bladder 118 to facilitate retention and alignment of the bladder on the neck support 128.

According to some embodiments, the second expandable bladder 118 is of a generally semi-ellipsoidal configuration having a relatively curved portion upon inflation for engaging a portion of the thoracic spine. Preferably, the second expandable bladder 118, when inflated, will expand about the same amount transversely and upwardly from the neck support 128. In some embodiments, the second expandable bladder 118 when inflated expands more transversely than upwardly. In some embodiments, the second expandable bladder 118 when inflated expands more upwardly than transversely. Thus, as the second expandable bladder 118 is inflated under and against the user's thoracic spine, it expands transversely and vertically, lifting the spine to counter hyper-kyphosis and applying an angular traction to the thoracic spine. The amount of traction exerted in the longitudial direction, preferably, will be similar to the amount of lift exerted vertically to obtain the necessary decompression and lift to restore the normal shape to the thoracic region of the spine.

In some embodiments, the second inflatable bladder 118 is constructed of an expandable material such as neoprene rubber, defines a length of between about 8 to 10 inches, a height of about 3 to 4 inches in an uninflated state, and depending on the configuration of the bladder a transverse width of about 3 inches. In some embodiments, the bladder 118 is constructed of a material that resists expansion. In some embodiments, the bladder 118 is constructed of a heat-sealable urethane with 200 Denier nylon. The bladder 118 can comprise a cover of any suitable material, including, for example, a neoprene material. The second inflatable bladder 118, when inflated, defines a transverse arc of about 4 inches in length about the center of the bladder. It is to be understood that these dimensions are by way of example only and can be varied without departing from the spirit and scope of the invention. For example, in some embodiments the bladder 118 can have a length of about 9 inches where it is coupled to the frame, a length of between about 6 and 7 inches where the bladder 118 contacts the patient. The bladder 118 can have a height of about 3 to 4 inches. The bladder 118 can have a circumference of about 6 to 7 inches.

In some embodiments the bladders preferably have a finite shape and expand while being filled until the bladders reach the finite shape. Once the bladder has been filled to the finite shape, the pressure release valve of the pump assembly allows for gas or fluid to escape from the system to maintain a desired pressure within the bladder. The pressure release valve is preferably an automatic pressure release valve. The system preferably also comprises a manual release valve, such as a push button release valve. The desired pressure is preferably held at a proven clinical level. In some embodiments the pressure release valve is configured to maintain a pressure of about 8 psi. At a pressure of about 8 psi the system preferably provides over 50 pounds of tractional force. In some embodiments the tractional force preferably is between about 50 and 60 pounds of tractional force.

While the above described bladder configurations are preferred, it is to be understood that other configurations of expandable bladders could be employed in the present invention, either with or without an expansion controlling casing to provide the desired lifting and traction of the user's neck and spine. Moreover, in some embodiments, mechanically expandable components can be used in place of the first and second bladders. Mechanically expandable components can be coupled to the frame and selectively expanded to applying force vectors to the cervical and thoracic spine in a manner similar to those produced by the expandable bladders as described herein. For example, in some embodiments an expanding mechanical component within a cushioned cover can be selectively actuated to provide the desired force distribution.

In some embodiments, one or more of the first and second expandable bladders 116, 118 are of a tubular configuration and are disposed in a non-expandable casing, preferably constructed of a vinyl or other suitable material. The casing is preferably formed in the above described generally ellipsoidal configurations. As the tubular bladder expands upon inflation, the expansion is limited by the configuration of the casing to provide the desired increase in the vertical and transverse directions.

Figure 8:
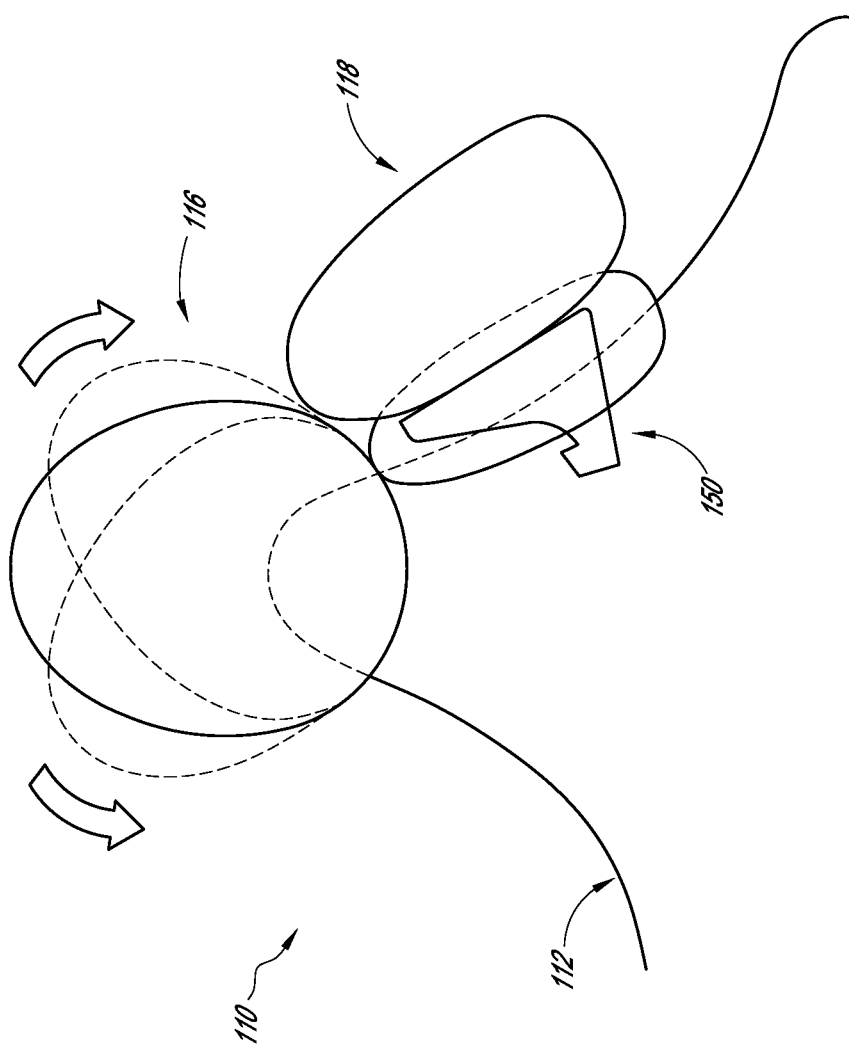
FIG. 8 is a schematic view of another embodiment of a decompression and traction system, showing mobile air cells comprising a first inflatable bladder being pivotably adjustable and showing a spacer component configured to be selectively coupled to the frame to adjust a position of a second inflatable bladder.

In some embodiments, as shown in FIG. 8, the first expandable bladder 116 is preferably rotatably secured to the neck support 128. The first expandable bladder 116 can be tilted in a forward position, a backward position, or maintained in a central position. In some embodiments, the bladder can be locked into a desired position. Providing a rotatable first expandable bladder 116 preferably provides mobility for the air cell to comfortably accommodate various spinal configurations. In some embodiments, the second expandable bladder 118 can be rotatably secured to the neck support 128.

In some embodiments, as shown in FIGS. 8 and 9, a spacer component 150 is preferably configured to be selectively coupled to the frame 112 to adjust a position of a second inflatable bladder 118. The spacer component can be attached to the frame and can allow clinicians and users to increase the negative Y directional component of the lower air cell. In one embodiment, the spacer component comprises an air cell or bladder engaging face 152, a notched connector portion 154 and opposing side portions 156. Other spacer configurations can be used to modify the directional component of the second inflatable bladder 118.

Figure 10A:
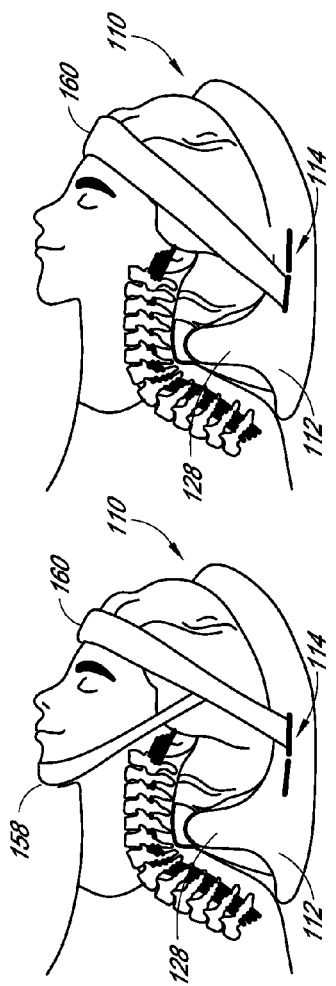
FIGS. 10A-F are illustrative views of a patient's spine in multiple configurations, including some embodiments of decompression and traction systems in use in deflated and inflated configurations.
Figure 10B:
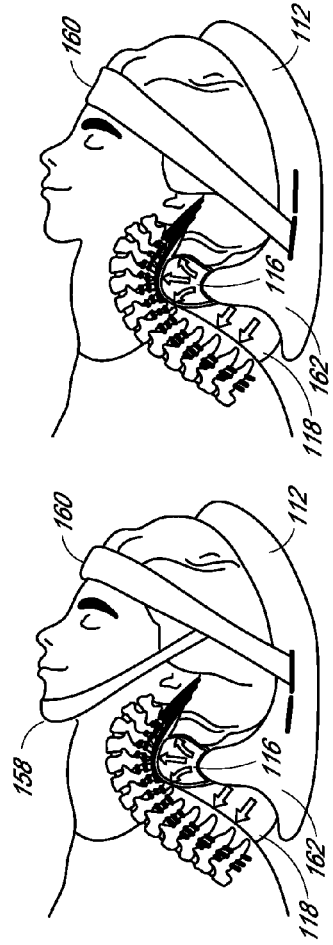
Figure 10C:
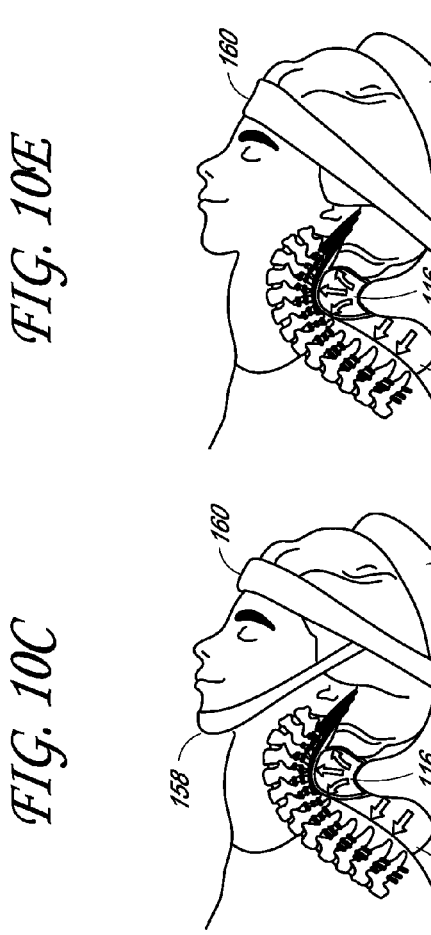
Figure 10D:
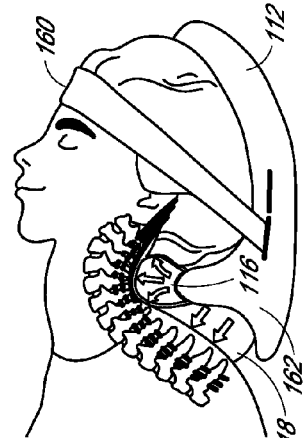
Figure 10E:
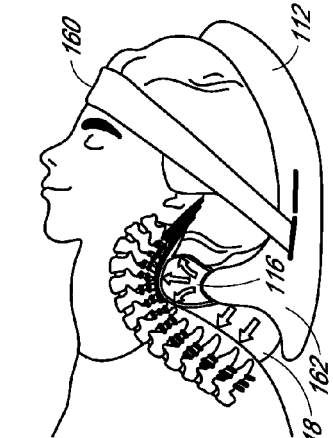
Figure 10F:
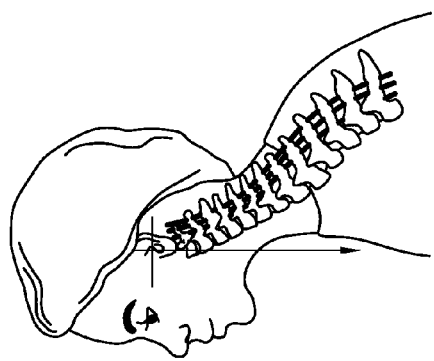

FIGS. 10A-F are illustrative views of a patient's spine in multiple configurations, including some embodiments of decompression and traction systems in use in deflated and inflated configurations. FIG. 10A shows a patient with cervical curve loss, forward head carriage, and disc compression. FIG. 10B shows a patient with normal spinal curves. FIGS. 10C and 10D show a patient and one embodiment of a decompression system 110 having a chin and forehead restraint, wherein the views show the decompression system 110 in a deflated configuration and an inflated configuration, respectively. FIGS. 10E and 10F show a patient and another embodiment of a decompression system 110 having a forehead restraint, wherein the views show the decompression system 110 in a deflated configuration and an inflated configuration, respectively.

As shown in FIGS. 10C-F, restraint straps 158 and/or 160 can be secured at the ends thereof to one or more of slots 114. Straps can be passed under the user's chin and over the user's forehead in some embodiments. In other embodiments, a strap can be passed over the user's forehead only. The straps can be secured and fastened in any suitable manner. For example, interlocking hook and loop type fasteners, snaps, buckles or other fasteners can be used. According to some embodiments, the traction device 110 can be easily and securely affixed to the user's head with a strap configuration such that with the user lying flat on his or her back on a horizontal surface, the frame 112 rests on the surface and the neck support 128 is disposed under the user's neck and tapered ends 162 of the frame side members 122, 124 are substantially adjacent the user's shoulders and generally near the upper thoracic region. The tightness of the securement of the device 110 to the user's head can be readily adjusted as needed by the securement straps 158, 160.

In some embodiments, the system preferably comprises a frame made of virgin acrylonitrile butadiene styrene (ABS) plastic material. ABS is an engineering thermoplastic that is advantageous due to its strength, toughness, chemical resistance, and ability to maintain necessary stiffness. The expandable air cells are preferably made of heat-sealable urethane with 200 Denier nylon. The expandable air cells preferably have a neoprene cover. The facial straps are preferably made of a durable and waterproof neoprene material. The hand pump and tubing are preferably made of rubber/plastic. Other embodiments can include different materials.

According to some embodiments, the system is lightweight (for example, about 3 lbs), portable, easy to operate, requires no assembly, no weights, cables or ropes to set-up, comes with choice of ballistic nylon carrying case or educational box, instruction page and instructional DVD. In one embodiment, the device comprises a built-in frame, an expanding elliptical air cell (with neoprene cover) that creates radial tractional force and thoracic decompressive force, a patient-controlled pneumatic hand pump with a push button release and automatic safety valve connected to approximately 30 inches of tubing, and one dual action head restraint designed for patients who suffer with TMJ (does not aggravate temporomandibular joint), which comprises an adjustable forehead strap, and a removable chin strap (which is optional in some other embodiments).

Accordingly to one aspect disclosed herein, methods for pneumatic radial traction can restore the cervical and thoracic spine to the proper configuration. Pneumatic radial traction, also known in some embodiments as expanding ellipsoidal decompression (EED), is a process in which joints of the cervical spine are pneumatically tractioned and simultaneously aligned into the cervical spine's proper radial or curved configuration. A major clinical difference between some embodiments of a pneumatic radial traction device disclosed herein and some prior art devices is that the prior art devices flatten or reverse the proper cervical curve to attain joint separation. In some embodiments, a pneumatic radial traction device enhances or maintains the proper cervical curve while attaining over twice the joint separation as some prior art devices.

With reference to FIGS. 10A and 10B, in the upright position, the cervical "lordotic" curve is what allows the weight of the head (10-15 lbs.) to be directed toward the hard boney posterior articular surfaces of the neck rather than toward the softer anterior discs as in the compressed neck. Through modern healthcare imaging it can be seen that that loss of the normal forward cervical curve (approx. 43°) and the resulting anterior disc compression this causes, was a contributing factor in osteophyte formation (Wolff's Law), posterior disc bulging, disc herniation, disc degeneration, neck pain and loss in cervical range of motion.

With reference to FIGS. 10C to 10F, pneumatic radial traction separates and simultaneously aligns the spinal joints in a curved or radial configuration. In some embodiments, an elliptical air cell directs multi-vectored expansive forces from within the posterior spinal concavity (back of neck), vertically (+Z axis translation) and in both horizontal directions. The spine is simultaneously tractioned in three main directions. The radial configuration created by these multi-vectored forces produces high level joint separation at the posterior, middle and anterior of the disc while forcefully enhancing the cervical spine's proper curve, rather than flattening or reversing the curve. Pneumatic radial traction is preferably achieved when the joints are separated by a vertical displacement greater than the horizontal displacement, however, displacement of equal height and width is also advantageous in some embodiments. An advantage of a pneumatic radial traction device is that it does not flatten or reverse the proper cervical curve while attaining joint separation. In some embodiments, the system provides a traction device with multiple fulcrums. For example, at least two fulcrums are provided to provide treatment to the cervical and thoracic spine of the patient.

As the head is stabilized in the cervical device, joints are actively tractioned in 3 main directions instead of one or two. The cervical spine is tractioned vertically along the +Z axis with a pneumatic force of over 58 lbs. This force expands into and against the posterior cervical concavity. Simultaneously the spine is tractioned horizontally in the two traditional directions (+Y and −Y) with a pneumatic force of over 40-lbs in each direction. These forces expand against the occiput and against the upper thoracic region. The combination of these simultaneously applied pneumatic forces produce radial traction. When fully inflated the elliptical pneumatic cell expands to a 7.5 inch radius, affecting the entire cervical spine. High level joint traction occurs at the posterior, center and anterior aspect of the vertebral bodies in a ratio coinciding with the discs' natural wedged spacing. While the pneumatic radial traction device separates the posterior of the joints to a magnitude typical of traditional traction, it separates the overall disc more than twice as much as linear traction.

With the simultaneous application of two separate air cells the cervical spine is decompressed into its proper lordotic or curved configuration (<Λ>) with −Y +Z +Y force vectors while the hyper kyphotic area of the upper thoracic spine is simultaneously decompressed with a combination +Z/−Y force mid-vector. The cervical spine's lordotic curve is powerfully decompressed and enhanced while the thoracic hyperkyphosis is simultaneously reduced.

Continuous expansion and contraction of the air cells can be employed to create alternating hydration and milking of the intervertebral discs, activating their sponge-like imbibition action. Holding the air pressure constant over a period of 15 to 20 minutes has the effect of simultaneously molding the spine into a curved or elliptical shape, decompressing discs and relaxing the dura, cord and nerve-roots in the cervical canal.

Embodiments described herein are preferably prescribed for patients with chronic neck pain due to a musculoskeletal or neurological impairment. The system applies radial tractional force to the cervical spine, enhancing the cervical lordotic curve while achieving high level joint separation at the anterior, center and posterior aspect of the vertebral bodies and discs in a ratio corresponding with their natural wedged spacing, reducing disc protrusions, compression and increasing range of motion. In some applications, devices advantageously decrease pain in chronic neck pain patients, decrease headaches and increase range of motion while reducing the necessity for chronic pain medication and neck surgery.

With continued reference to FIGS. 10A-10F, according to some embodiments in use, the traction device 110 rests on a horizontal surface such that the neck support 128 projects upwardly therefrom. The user lies on the device in a prone position such that the back of the neck rests on the deflated first expandable bladder 116 carried in the cradle 138 of the neck support 128. The deflated second expandable bladder 118 is positioned between the neck support 128 and portions of the thoracic spine of the user. The chin and/or forehead restraining restraint straps are respectively extended under the user's chin and/or about the user's forehead and secured, thereby affixing the traction device 110 to the user such that the neck and cervical spine extend over the neck support and first expandable bladder 116 and the thoracic spine is adjacent the second expandable bladder 118. According to one preferred embodiment, the outward extension of the neck support 128 is relatively slight so that when the bladder is in the deflated position with the forehead and chin restraints secured, very little or no force is exerted on the neck by the neck support. This is achieved by elevating the neck support 128 above the frame such that the neck cradle 138 formed therein is about 2 to 3 inches above the floor or other horizontal surface on which the device 110 is used. The first expandable bladder 116 is sized such that upon full inflation, the apex of the curved upper surface of the bladder will extend about 5 inches above the floor or surface. The second expandable bladder 118 is sized such that upon full inflation, a surface of the second expandable bladder engaging the thoracic spine will extend toward the thoracic spine about 2 to 3 inches in the −Y/+Z direction.

In some embodiments, as the user slowly inflates the first and second inflatable bladders 116, 118 using the air pump 142, the first inflatable bladder 116 expands upwardly and, to a lesser extent, transversely, thereby forcing the cervical spine forwardly creating a spinal apex while concurrently stretching the spine angularly along both sides of the formed spinal apex. The second inflatable bladder 118 expands transversely in the −Y direction, thereby forcing the thoracic spine forwardly to offset the effects of hyper-khyphosis. The user then continues to inflate the first and second bladders 116 and 118 until his or her individual tolerance level is reached. The bladders are then deflated by use of the one way valve 144. The process is preferably repeated several times, slowly increasing the spinal arc in the cervical region and placing pressure on the thoracic region as the level of tolerance increases. In addition, the first and second bladders 116 and 118 can be held in an inflated state at or slightly below the level of tolerance for varying periods of time up to ten to twenty minutes. Through such repetition, the cervical spine, thoracic spine and surrounding tissue receive a workout promoting cellular exchange in and around the intervertebral disc and a forward curve is reinstated into the cervical spine while achieving proper spine configuration in the thoracic region. FIGS. 10A-10F illustrate the effects of the traction and exercise devices 110 of some embodiments on the cervical and thoracic spine.

The various devices, systems and methods described above provide a number of ways to carry out some preferred embodiments of the invention. Of course, it is to be understood that not necessarily all objectives or advantages described may be achieved in accordance with any particular embodiment described herein. Thus, for example, those skilled in the art will recognize that the devices and systems may be made and the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various components, features and steps discussed above, as well as other known equivalents for each such component, feature or step, can be mixed and matched by one of ordinary skill in this art to make devices and systems and perform methods in accordance with principles described herein.

Although the invention has been disclosed in the context of some embodiments and examples, it will be understood by those skilled in the art that the invention extends beyond these specifically disclosed embodiments to other alternative embodiments and/or uses and obvious modifications and equivalents thereof. Accordingly, the invention is not intended to be limited by the specific disclosures of preferred embodiments herein.

What is claimed is:

1. A traction device for imparting a forward curve to the cervical spine and reducing hyper-kyphosis of the upper thoracic spine, the device comprising:
   a frame adapted to be supported on a rigid support surface, the frame configured to be disposed about a user's head and neck and defining contact surfaces for abutting the rigid support surface, the frame having a neck support extending between first and second side portions of the frame;
   a first inflatable elongated bladder coupled to the neck support and configured to be positioned below a neck of a user during use, the first inflatable elongated bladder being expandable in a first direction outwardly from the neck support toward the neck of a user and expandable in a second direction substantially normal to the first direction upon inflation;
   a second inflatable elongated bladder coupled to the neck support and configured to be positioned below the upper thoracic region of a user during use, the second inflatable elongated bladder being expandable in a third direction angularly from the neck support toward the upper thoracic spine of a user upon inflation;
   a securing strap coupled to the frame and configured to secure the frame to the user's head such that the first inflatable elongated bladder is disposed adjacent the back of the user's neck and transverses the cervical spine such that the first direction of expansion is toward and substantially normal to the cervical spine, and such that the second inflatable elongated bladder is disposed adjacent the back of the user's upper thoracic region and transverses the upper thoracic spine such that the third direction of expansion is toward and substantially normal to the upper thoracic spine; and
   a pump system for selectively inflating and deflating the first and second inflatable elongated bladders, whereby upon the first inflatable bladder expanding in the first direction, the first inflatable bladder bears outwardly against the back of the user's neck as the first inflatable bladder is inflated and forces the cervical spine to curve forwardly, and upon expanding in the second direction, the first inflatable bladder applies an angular traction to the cervical spine and, whereby upon the second inflatable bladder expanding in the third direction, the second inflatable bladder bears angularly against the back of the user's upper thoracic region and forces the thoracic spine to decompress and reduces hyper-kyphosis of the upper thoracic spine.

2. The device of claim 1 wherein the first inflatable elongated bladder is expandable in the first direction a greater distance than the first inflatable elongated bladder is expandable in the second direction.

3. The device of claim 1 wherein a lower portion of the first inflatable elongated bladder is disposed adjacent the neck support and defines a depending central portion for causing the first inflatable elongated bladder to expand outwardly from the neck support in the first direction a distance greater than the expansion of the first inflatable elongated bladder is in the second direction, an upper portion of the first inflatable elongated bladder being substantially semi-ellipsoidal in configuration upon inflation.

4. The device of claim 1, comprising a valve positioned in communication with the pump system and the first and second inflatable elongated bladders, wherein the valve comprises varying lumen diameters that direct flow between the pump system and the first and second inflatable elongated bladders.

5. The device of claim 1, wherein the first inflatable elongated bladder is pivotably coupled to the neck support.

6. The device of claim 1, comprising a spacer configured to be coupled between a portion of the frame and the second inflatable elongated bladder to adjust the angulation of the second inflatable elongated bladder during inflation.

7. A traction device for imparting a forward curve to the cervical spine and reducing hyper-kyphosis of the upper thoracic spine, the device comprising:
- a frame having a transverse neck support projecting upwardly from first and second side portions defining a base of the frame;
- a first inflatable bladder portion coupled to the neck support, the first inflatable bladder portion configured to expand in an outward direction from the neck support a distance greater than the expansion of the first inflatable bladder portion in a transverse direction normal thereto;
- a second inflatable bladder portion coupled to the neck support, the second inflatable bladder portion configured to expand in an angular direction from the neck support, the second inflatable bladder portion being positioned generally below and to the side relative to the first inflatable bladder portion;
- a strap coupled to the frame and configured to secure the frame to the user's head such that the first inflatable bladder portion is disposed adjacent the back of the user's neck and transverses the cervical spine such that the outward direction of expansion is toward and substantially normal to the cervical spine, and such that the second inflatable bladder portion is disposed adjacent the back of the user's upper thoracic region and transverses the upper thoracic spine such that the angular direction of expansion is toward and substantially normal to the upper thoracic spine; and
- a pump system for inflating the first and second inflatable bladder portions, whereby upon the first inflatable bladder portion expanding in the outward direction, the first inflatable bladder portion bears outwardly against the back of the user's neck and forces the cervical spine to curve forwardly, and upon expanding in the transverse direction, the first inflatable bladder portion applies an angular traction to the cervical spine and, whereby upon the second inflatable bladder portion expanding in the angular direction, the second inflatable bladder portion bears angularly against the back of the user's upper thoracic region and forces the thoracic spine to decompress and reduces hyper-kyphosis of the upper thoracic spine.

8. The device of claim 7 wherein a lower portion of the first inflatable bladder portion is disposed adjacent the neck support and defines a depending central portion for causing the first inflatable bladder portion to expand outwardly from the neck support in the outward direction a distance greater than the expansion of the first inflatable bladder portion is in the second direction, an upper portion of the first inflatable bladder portion being substantially semi-ellipsoidal in configuration upon inflation.

9. The device of claim 7 comprising a valve positioned in communication with the pump system and the first and second inflatable bladder portions, wherein the valve comprises different lumen diameters that direct flow between the pump system and the first and second inflatable bladder portions.

10. The device of claim 7, wherein the first inflatable bladder portion is pivotably coupled to the neck support.

11. The device of claim 7, comprising a spacer configured to be coupled between a portion of the frame and the second inflatable bladder portion to adjust the angulation of the second inflatable bladder portion during inflation.

\* \* \* \* \*